US00PP16835P2

(12) United States Plant Patent
Egger

(10) Patent No.: US PP16,835 P2
(45) Date of Patent: Jul. 18, 2006

(54) ×***HEUCHERELLA* PLANT NAMED 'STOPLIGHT'**

(50) Latin Name: ×***Heucherella* sp.**
Varietal Denomination: Stoplight

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 67 days.

(21) Appl. No.: 11/045,832

(22) Filed: Jan. 27, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct cultivar of ×*Heucherella* plant characterized by its distinctive gold to chartreuse foliage with a large, starry, maroon blotch.

1 Drawing Sheet

Botanical denomination: ×*Heucherella* sp.
Variety designation: 'Stoplight'.

BACKGROUND OF THE INVENTION

The present invention relates to a new and distinct intergeneric hybrid between *Heuchera* and *Tiarella,* or ×*Heucherella,* and given the cultivar name 'Stoplight'. Both genera, *Heuchera* and *Tiarella,* are of the family Saxifragaceae.

This new cultivar was bred using *Heuchera* AWH-12, a proprietary, unreleased plant as the seed parent and *Tiarella* BL2, a proprietary, unreleased plant as the pollen parent.

SUMMARY OF THE INVENTION

This new ×*Heucherella* is unique in its bright golden to chartreuse foliage with a very large maroon blotch in the center and characterized by:

1. Large, shallowly lobed leaves.
2. Unusual white flowers.

The new variety has been reproduced only by asexual propagation (division and tissue culture). Each of the progeny exhibits identical characteristics to the original plant. Asexual propagation by division and tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows the one year old plant of the new variety growing in a one-gallon pot surrounded by various *Heuchera* with dark and silver leaves in Canby, Oreg.

DETAILED PLANT DESCRIPTION

The following is a detailed description of the new ×*Heucherella* hybrid based on observations of one-year-old specimens grown in a one-gallon pot in a cold greenhouse in Canby, Oreg. This greenhouse is kept at between 55 and 85 degrees F. in the summer months and in the winter is heated to frost free, above 32 degrees F. and vented at 55 degrees F. Light intensities are consistent with full sun in Canby, Oreg. which gets 42.8 inches of rain per year and is often cloudy. Plants were hand watered when dry. The color descriptions are all based on The Royal Horticultural Society Colour Chart.

Plant:
- *Type.*—Herbaceous perennial.
- *Form.*—Basal rosette.
- *Hardiness.*—USDA Zone 5.
- *Size.*—15 cm tall from the soil to the top of the foliage and 35 cm wide.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Broadly ovate, becoming cupped and rugose with age.
- *Lobing/Division.*—5 shallow main lobes with each of these shallowly lobed.
- *Venation*—Palmate.
- *Margins.*—Crenate.
- *Apex.*—Acute.
- *Base.*—Cordate.
- *Blade size.*—Ranges from 9 to 12.5 cm long and 8.5 to 10.5 cm wide.
- *Surface texture.*—Hispid and with glandular hairs.
- *Petiole size.*—Ranges from 9 to 11 cm long and 1.5 to 2 mm wide.
- *Petiole texture.*—Hispid and with glandular hairs.
- *Petiole color.*—Closest to Greyed Purple 185C and lightening to Yellow Green 150D near leaf blade.

*Leaf color.*—Leaves open in spring a yellow green with a dark red center pattern and become more yellow with maturity. New spring leaves topside — Between Yellow Green 154A and Yellow Green 151A with slightly more green. Reddish pattern in the center and following the veins, Greyed Purple 187B. Mature spring leaves topside — Yellow 8B with faint yellow green on veins to Yellow 5D, both with the center Greyed Purple 185A. Spring leaves — bottom side — Yellow 5D. Summer leaves — topside — Between Yellow Green 144A and Yellow Green 146B with the reddish pattern along the veins, Greyed Purple 187B. Winter leaves — Red brown tinged where most exposed, Greyed Orange 176A.

Inflorescence:

*Type.*—Thyrse.

*Number of flowers.*—Ranges from 60 to 70 per thyrse.

*Number of thryse in spring flush.*—8.

*Size of inflorescence.*—13 cm long and 3 cm wide.

*Peduncle.*—With 2 leaves and branches, height 42 cm, width 2 mm, Greyed Purple 183A and lighter toward tip, Yellow 5D or Greyed Yellow 160A, pubescent.

*Pedicel.*—Grows to 5 mm long and 1 mm wide, pubescent, Greyed Purple 185C.

*Bloom period.*—Early April to late May.

Flower bud:

*Size.*—3 mm deep and wide.

*Description.*—Ovoid, side facing, pubescent.

*Color.*—Greyed Yellow 161B.

Flower:

*Type.*—Perfect, sepals petaloid.

*Shape.*—Rotate.

*Size.*—6 to 7 mm wide and deep.

*Petal description.*—5 in number, 2.5 mm long and 1 mm wide, oblanceolate in shape, margins entire, apex acute, White 155D.

*Calyx description.*—Petaloid, rotate in shape, 7 mm wide and 1.5 mm deep, 5 lobes divided ¾ of the way to the base, waxy and with glandular hairs on the outside, glabrous inside, margins entire, apices acute.

*Calyx color.*—Outside: White 155D with touches of pink, Greyed Purple 186D. Inside: White 155D.

*Stamen description.*—5 in number, 2.5 mm long, thickened, sterile, White 155A.

*Pistil description.*—One, White 155D, 3.5 mm long.

*Fragrance.*—None.

*Lastingness.*—A thyrse blooms for about 2 weeks on the plant.

Fruit and seed: None. The plant does not form fruit or seed.

*Fertility.*—Sterile.

Disease and pest tolerance: All ×*Heucherella* are susceptible to root weevils. No problems have been identified for this new cultivar.

COMPARISONS TO SIMILAR ×*HEUCHERELLA*

Compared to ×*Heucherella* 'Sunspot' (U.S. Plant Pat. No. 14,825), this new cultivar has leaves that are larger, with more intense coloring, 5 rather than 3 main lobes, and white, rather than pink flowers.

The seed parent *Heuchera* AWH-12 had tan-colored foliage. The pollen parent *Tiarella* BL2 was a well marked broad leaf *Tiarella*. *Heucherella* 'Stoplight' has broad leaves like both parents and the well marked dark center of the pollen parent.

I claim:

1. A new and distinct cultivar of ×*Heucherella* plant as herein illustrated and described.

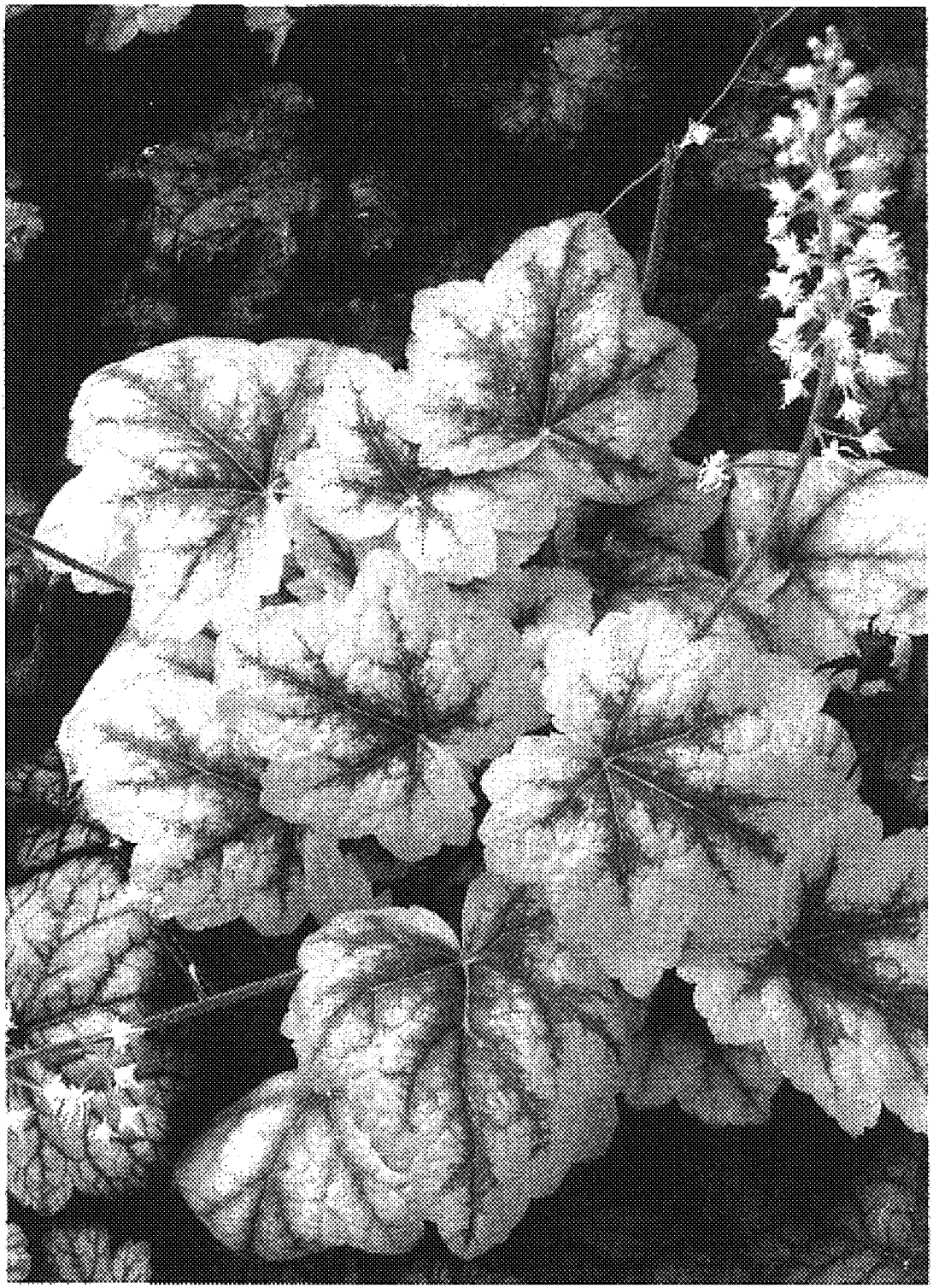

* * * * *